United States Patent
O'Lenick, Jr. et al.

(10) Patent No.: US 6,252,107 B1
(45) Date of Patent: Jun. 26, 2001

(54) CARBOXY AMPHOTERIC SURFACTANT COMPLEXES

(76) Inventors: Anthony J. O'Lenick, Jr., 2170 Luke Edwards Raod, Dacula, GA (US) 30019; Charles W. Buffa, 510 E. 37th St., Paterson, NJ (US) 07450

( * ) Notice: Subject to any disclaimer, the term of this patent is extended or adjusted under 35 U.S.C. 154(b) by 0 days.

(21) Appl. No.: 09/483,004

(22) Filed: Jan. 18, 2000

(51) Int. Cl.$^7$ .................................................. C07C 331/00
(52) U.S. Cl. .......................................... 560/302; 562/433
(58) Field of Search ............................... 560/302; 562/433

(56) References Cited

U.S. PATENT DOCUMENTS 3,417,136 * 12/1968 Hovden ................................. 260/534
5,739,371 * 4/1998 O'Lenick, Jr. ....................... 556/418

* cited by examiner

*Primary Examiner*—Porfirio Nazario-Gonzalez

(57) ABSTRACT

The present invention is directed to a class of compounds that are made by neutralizing the amino group in an amphoteric surfactant with the carboxylic acid group. The complex has (a) lower irritation, (b) better foaming properties and (c) improved substantivity to a variety of substrates.

17 Claims, No Drawings

CARBOXY AMPHOTERIC SURFACTANT COMPLEXES

FIELD OF THE INVENTION

The present invention is directed to a class of compounds that are made by neutralizing the amino group in an amphoteric surfactant with the carboxylic acid group in an alkoxylated fatty alcohol compound. The complex has (a) lower irritation, (b) better foaming properties and (c) improved substantivity to a variety of substrates.

BACKGROUND OF THE INVENTION

The present invention relates to specific salts of amphoteric surfactants and carboxy fatty compounds. The compounds have unique properties including high foam, detergency and most importantly low irritation to the eye and skin. This makes the compounds of the present invention particularly well suited for personal care applications. Additionally, the compounds of the present invention are useful in industrial applications where detergency and substantivity are required. One particular application is in metal cleaning and corrosion inhibition. The compounds of the present invention provide both detergency and corrosion inhibition when applied to metal surfaces.

Amphoteric surfactants have been known for many years. The amphoteric compounds useful in the preparation of the compounds of the present invention are amino propronates. U.S. Pat. No. 3,417,136 to Hovoden describes the basic technology used to make amphoteric surfactants of the class which is useful for the preparation of the complexes of the present invention.

Silicone carboxy complexes are disclosed in U.S. Pat. No. 5,739,371 issued April 1998 to O'Lenick, incorporated herein by reference. That specific patent disclosed that silicone polymers were needed to observe the beneficial effects observed. We have now surprisingly observed that the same effect is obtained using fatty alcohol carboxylates in place of silicone carboxylates. This has very far reaching impact upon cost and formulation latitude in personal care products.

SUMMARY OF THE INVENTION

The compounds of the present invention are salts of an amphoteric and an alkoxylated alkyl carboxylate. The preparation of the specific salt compounds of the present invention results in properties heretofore unattainable. Specifically, the fatty amphoteric compounds of the present invention are good detergents, but are somewhat irritating to the skin and eyes. This irritation results in a defatting of the skin and an unacceptable feel on the skin. The alkoxylated alkyl carboxylate per se is neither a good detergent nor very mild to the skin. Surprisingly, both together in a salt of the present invention, the compounds of the present invention are very mild to skin and eye, and possess outstanding detergency. This combination of properties make compounds of the present invention applicable many personal care applications, where the cost of silicone is prohibitive.

Another very useful application for the salts of the present invention is in two in one shampoos. If one makes a complex of a standard fatty quaternary compound and a standard fatty anionic surfactant, the resulting salt is water insoluble and of very little usefulness in either cleaning or conditioning hair. The salts of the present invention are water soluble and unexpectedly provide both detergency and conditioning to the hair in a single application.

OBJECT OF THE INVENTION

It is the object of the present invention to provide a series of amphoteric/carboxy salts. These compounds have an outstanding combination of properties making them useful in personal care, and industrial applications. Another aspect of the present invention is a process for using the compounds of the present invention in cleaning and conditioning hair with the application of a single compound.

DETAILED DESCRIPTION OF THE INVENTION

The amphoteric surfactants from which the compounds of the present invention are based have the following structure:

$R^3$ is selected from the group selected from $CH_3$—$(CH_2)$d— and $CH_3$—$(CH_2)_e$—O—;

d is an integer ranging from 7 to 19;

e is an integer ranging from 7 to 19;

M is selected from Na, K, and Li.

The nitrogen group in the molecule is a tertiary amine and can be neutralized with a carboxylic acid. Such an acid is the alkoxylated acid useful in the preparation of the compounds of the current invention. The reaction is a neutralization reaction and can be explained by the following reaction sequence:

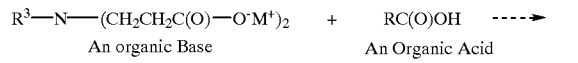
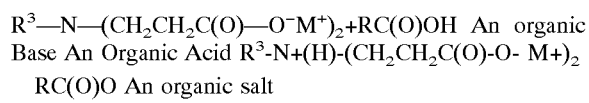

$R^3$—N—$(CH_2CH_2C(O)$—$O^-M^+)_2$+$RC(O)OH$ An organic Base An Organic Acid $R^3$-N+(H)-$(CH_2CH_2C(O)$-O- M+$)_2$ $RC(O)O$ An organic salt The compounds of the present invention are salts which conform to the following structure:

$$A^-B^+$$

wherein

A is $R^1$—O—C(O)—$R^2$—C(O)O $R^1$ is $CH_3$—$(CH_2)_n$—O—$(CH_2CH_2O)_a$—$(CH_2CH(CH_3)O)_b$—$(CH_2CH_2O)_c$—;

n is an integers ranging from 7 to 21;

a and c are integers independently ranging from 0 to 20, with the proviso that a+b be greater than 5;

b is an integer ranging from 0 to 20;

$R^2$ is selected from the group consisting of

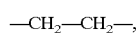

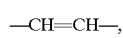

and

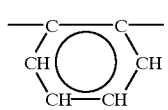

and B is

$R^3$ is selected from the group selected from $CH_3—(CH_2)_d—$ and $CH_3—(CH_2)_e—O—$;

d is an integer ranging from 7 to 19;

e is an integer ranging from 7 to 19:

M is selected from Na, K, and Li.

Preferred Embodiments

In a preferred embodiment R3 is $CH_3—(CH_2)_d—$.

In another preferred embodiment R3 is $CH_3—(CH_2)_e—O—$.

In a preferred embodiment d is 7.
In a preferred embodiment d is 9.
In a preferred embodiment d is 11.
In a preferred embodiment d is 13.
In a preferred embodiment d is 15.
In a preferred embodiment d is 17.
In a preferred embodiment d is 19.
In a preferred embodiment e is 7.
In a preferred embodiment e is 9.
In a preferred embodiment e is 11.
In a preferred embodiment e is 13.
In a preferred embodiment e is 15.
In a preferred embodiment e is 17.
In a preferred embodiment e is 19.

EXAMPLES OF REACTANTS

Anhydrides

The various anhydrides listed are all items of commerce and are prepared by methods known to those skilled in the art.

Reactant Example I (Succinic Anhydride)

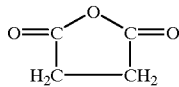

Reactant Example II ( Maleic Anhydride)

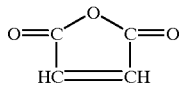

Reactant Example III (Phthalic Anhydride)

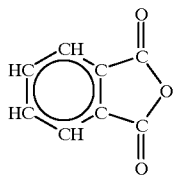

Alcohol Alkoxy Carboxylate

The reaction sequence is illustrated by the reaction with succinic anhydride:

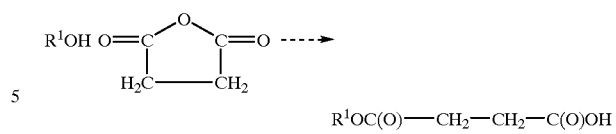

Raw Materials

Alkoxylated alcohols suitable for the preparation of the compounds of the present invention are commercially available from Siltech Corporation in Toronto Ontario Canada.

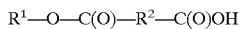

| Example | n | a | b | c |
|---|---|---|---|---|
| 1 | 8 | 0 | 0 | 5 |
| 2 | 10 | 0 | 1 | 12 |
| 3 | 12 | 20 | 10 | 20 |
| 4 | 14 | 3 | 1 | 3 |
| 5 | 16 | 20 | 20 | 20 |
| 6 | 18 | 12 | 0 | 0 |
| 7 | 20 | 12 | 1 | 1 |
| 8 | 22 | 5 | 0 | 5 |

General Reaction Conditions

Into a suitable round bottom, three neck flask equipped with a thermometer and a nitrogen sparge is added the specified number of grams of the specified alcohol alkoxylate compound and the specified number of grams of the specified anhydride. The reaction mass is blanketed with nitrogen, and heated to 80 and 110 C. under the inert nitrogen blanket. Within four to five hours the theoretical acid value is obtained. The product is a clear liquid and is used without additional purification.

Examples 9–18

Succinic Derivatives

Into a suitable round bottom, three neck flask equipped with a thermometer and a nitrogen sparge is added the specified number of grams of the specified alcohol alkoxylate (examples 1—8) compound and the 100.0 grams of succinic anhydride. The reaction mass is blanketed with nitrogen, and heated to 80 and 110 C. under the inert nitrogen blanket. Within four to five hours the theoretical acid value is obtained. The product is a clear liquid and is used without addition purification.

| | Alcohol Alkoxylate | |
|---|---|---|
| Example | Example | Grams |
| 9 | 1 | 391.0 |
| 10 | 2 | 742.0 |
| 11 | 3 | 2533.0 |
| 12 | 4 | 447.0 |
| 13 | 5 | 3179.0 |
| 14 | 6 | 795.0 |
| 15 | 7 | 926.0 |
| 16 | 8 | 763.0 |

Examples 17–24

Maleic Derivatives

Into a suitable round bottom, three neck flask equipped with a thermometer and a nitrogen sparge is added the specified number of grams of the specified alcohol alkoxylate (examples 1–8) compound and the 98.0 grams of maleic anhydride. The reaction mass is blanketed with nitrogen, and heated to 80 and 110 C. under the inert nitrogen blanket. Within four to five hours the theoretical acid value is obtained. The product is a clear liquid and is used without additional purification.

|  | Alcohol Alkoxylate | |
|---|---|---|
| Example | Example | Grams |
| 17 | 1 | 391.0 |
| 18 | 2 | 742.0 |
| 19 | 3 | 2533.0 |
| 20 | 4 | 447.0 |
| 21 | 5 | 3179.0 |
| 22 | 6 | 795.0 |
| 23 | 7 | 926.0 |
| 24 | 8 | 763.0 |

Examples 25–32

Phthalic Derivatives

Into a suitable round bottom, three neck flask equipped with a thermometer and a nitrogen sparge is added the specified number of grams of the specified alcohol alkoxylate (examples 1–8) compound and the 146.0 grams of phthalic anhydride. The reaction mass is blanketed with nitrogen, and heated to 80 and 110 C. under the inert nitrogen blanket. Within four to five hours the theoretical acid value is obtained. The product is a clear liquid and is used without additional purification.

|  | Alcohol Alkoxylate | |
|---|---|---|
| Example | Example | Grams |
| 25 | 1 | 391.0 |
| 26 | 2 | 742.0 |
| 27 | 3 | 2533.0 |
| 28 | 4 | 447.0 |
| 29 | 5 | 3179.0 |
| 30 | 6 | 795.0 |
| 31 | 7 | 926.0 |
| 32 | 8 | 763.0 |

Amphoteric Surfactants $$R^3\text{—}N\text{—}(CH_2CH_2C(O)\text{—}O^-M^+)_2$$

$R^3$ is selected from the group selected from $CH_3\text{—}(CH_2)_d\text{—}$ and $CH_3\text{—}(CH_2)_e\text{—}O\text{—}$;

M is selected from Na, K, and Li;

d is an integer ranging from 7 to 19;

e is an integer ranging from 7 to 19;

Class 1 (Alkyl Amphoteric)

$R^3$ is 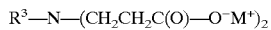

The amphoteric surfactants of this class are commercially available from a variety of sources including Henkel Corporation. These products are available at a variety of actives. Therefore all were adjusted to 30% actives prior to use. Consequently, the grams listed in the examples for these materials is based upon 30% actives.

| Example | M | d |
|---|---|---|
| 33 | Na | 7 |
| 34 | K | 9 |
| 35 | Na | 11 |
| 36 | Li | 13 |
| 37 | Na | 15 |
| 38 | K | 17 |
| 39 | Na | 19 |

Class 2 (Alkyl Ether Amphoteric)

Compounds of this class are commercially available from a variety of sources, most importantly Tomah Products of Milton Wis. These products are available at a variety of actives. Therefore all were adjusted to 30% actives consequently, the grams listed in the examples materials is based upon 30% actives.

$R^3$ is $CH_3\text{—}(CH_2)_3\text{—}O\text{—}$;

| Example | M | e |
|---|---|---|
| 40 | Na | 7 |
| 41 | K | 9 |
| 42 | Na | 11 |
| 43 | Li | 13 |
| 44 | Na | 15 |
| 45 | K | 17 |
| 46 | Na | 19 |

Examples

The compounds of the present invention are prepared by the mixing of the amphoteric surfactant and the carboxy compounds, preferably in aqueous solution, resulting in the neutralization of the compounds and preparation of the salts of the current invention.

Example 47

1136.0 grams amphoteric compound at 30% Active (example 33) is added to a suitable vessel. Next 391.0 the specified carboxy (example 9) is added under good agitation. Water is then added to adjust the solids to 40%. The resulting salt is ready to use without additional purification. The compounds can be prepared in aqueous solution if desired by addition of water. Preferred concentrations are between 50% and 30% amphoteric solids by weight.

Note: In the below table Gms. is grams

Examples 48–79

|  | Carboxy Compound | | Amphoteric Compound | |
|---|---|---|---|---|
| Example | Example | Grams | Example | Grams |
| 48 | 11 | 2533.0 | 37 | 1510.0 |
| 50 | 12 | 447.0 | 38 | 1710.2 |
| 51 | 13 | 3179.0 | 39 | 1697.0 |
| 52 | 14 | 795.0 | 40 | 1190.0 |
| 53 | 15 | 926.0 | 41 | 1390.0 |
| 54 | 16 | 763.0 | 42 | 1270.0 |

-continued

| Example | Carboxy Compound Example | Grams | Amphoteric Compound Example | Grams |
|---|---|---|---|---|
| 55 | 17 | 391.0 | 43 | 1470.0 |
| 56 | 18 | 742.0 | 44 | 1563.0 |
| 57 | 19 | 2533.0 | 45 | 1656.0 |
| 58 | 20 | 447.0 | 46 | 1750.0 |
| 59 | 21 | 3179.0 | 33 | 1136.6 |
| 60 | 22 | 795.0 | 34 | 1336.2 |
| 61 | 23 | 926.0 | 35 | 1323.0 |
| 62 | 24 | 763.0 | 36 | 1370.0 |
| 63 | 25 | 391.0 | 33 | 1136.6 |
| 64 | 26 | 742.0 | 34 | 1336.0 |
| 65 | 27 | 2533.0 | 35 | 1323.0 |
| 66 | 28 | 447.0 | 36 | 1310.0 |
| 67 | 29 | 3179.0 | 37 | 1510.0 |
| 68 | 30 | 795.0 | 38 | 1710.2 |
| 69 | 31 | 926.0 | 39 | 1697.0 |
| 70 | 32 | 763.0 | 40 | 1190.0 |
| 71 | 10 | 742.0 | 36 | 1310.0 |
| 72 | 9 | 391.0 | 36 | 1310.0 |

Applications Examples

The compounds of the present invention are low irritation surface active agents which exhibit good detergency and foam properties. This combination of properties makes the compounds useful in personal care applications. The following data illustrates the desirable properties of the salts which are lacking in either component alone.

|  | Amphoteric Example 33 | Carboxy Example 1 | Complex Ex 47 |
|---|---|---|---|
| Eye Irritation | Moderate | Mild | Mild |
| Detergency | Good | Poor | Good |
| Foam | Good | Poor | Good |

What is claimed:

1. A carboxy amphoteric complex which conforms to the following structure:

$$A^- B^+$$

wherein

A is $R^1$—O—C(O)—$R^2$—C(O)O $R^1$ is $CH_3$—$(CH_2)_n$—O—$(CH_2CH_2O)_a$—$(CH_2CH(CH_3)O)_b$—$(CH_2CH_2O)_c$—;

n is an integers ranging from 7 to 21;

a and c are integers independently ranging from 0 to 20, with the proviso that a+b be greater than 5;

b is an integer ranging from 0 to 20;

$R^2$ is selected from the group consisting of

—$CH_2$—$CH_2$—,

—CH=CH—, and

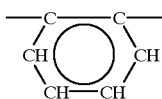

and B is $R^3$—$N^+$(H)—$(CH_2CH_2C(O)O^- M^+)_2$ $R^3$ is selected from the group selected from $CH_3$—$(CH_2)_d$— and $CH_3$—$(CH_2)_e$—O—;

d is an integer ranging from 7 to 19;

e is an integer ranging from 7 to 19;

M is selected from Na, K, and Li.

2. A compound of claim 1 wherein R2 is $CH_3$—$(CH_2)_a$—.

3. A compound of claim 1 wherein R2 is $CH_3$—$(CH_2)_b$—O—.

4. A compound of claim 2 wherein a is 7.
5. A compound of claim 2 wherein a is 9.
6. A compound of claim 2 wherein a is 11.
7. A compound of claim 2 wherein a is 13.
8. A compound of claim 2 wherein a is 15.
9. A compound of claim 2 wherein a is 17.
10. A compound of claim 2 wherein a is 19.
11. A compound of claim 3 wherein b is 7.
12. A compound of claim 3 wherein b is 9.
13. A compound of claim 3 wherein b is 11.
14. A compound of claim 3 wherein b is 13.
15. A compound of claim 3 wherein b is 15.
16. A compound of claim 3 wherein b is 17.
17. A compound of claim 3 wherein b is 19.

* * * * *